United States Patent [19]

Geisler et al.

[11] Patent Number: 4,847,196

[45] Date of Patent: Jul. 11, 1989

[54] STABILIZED COMPOSITION OF TETRAZOLIUM SALTS

[75] Inventors: Edda Geisler, Mannheim; Helmut Feuerstein, Mannheim-Ilvesheim; Hans Lange, Lampertheim, all of Fed. Rep. of Germany

[73] Assignee: Boehringer Mannheim GmbH, Mannheim, Fed. Rep. of Germany

[21] Appl. No.: 147,568

[22] Filed: Jan. 19, 1988

Related U.S. Application Data

[60] Continuation of Ser. No. 871,498, Jun. 6, 1986, abandoned, which is a division of Ser. No. 593,192, Mar. 27, 1984, Pat. No. 4,613,569, which is a continuation of Ser. No. 328,315, Dec. 7, 1981, abandoned.

[30] Foreign Application Priority Data

Dec. 23, 1980 [DE] Fed. Rep. of Germany ....... 3048662

[51] Int. Cl.[4] ............. G01N 1/48; G01N 53/00; G01N 1/00; C12Q 1/32
[52] U.S. Cl. ............................. 435/26; 422/56; 436/129; 436/176; 436/903
[58] Field of Search .............. 436/93, 95, 97, 176, 436/903, 904; 422/56; 435/26; 548/250

[56] References Cited

U.S. PATENT DOCUMENTS

| | | | |
|---|---|---|---|
| 3,676,135 | 7/1972 | Musliner | 430/367 |
| 3,732,147 | 5/1973 | Fosker et al. | 435/26 |
| 3,867,259 | 2/1975 | Forgione | 435/26 |
| 3,957,514 | 5/1976 | Adin | 548/26 |
| 4,056,485 | 2/1976 | Adolf et al. | 435/26 |
| 4,152,116 | 5/1979 | Deneke et al. | 436/93 |
| 4,613,569 | 3/1984 | Geisler et al. | 436/93 |

Primary Examiner—Barry S. Richman
Assistant Examiner—Lyle Alfandary-Alexander
Attorney, Agent, or Firm—Felfe & Lynch

[57] ABSTRACT

The present invention provides stabilized compositions of tetrazolium salts for analytical purposes which contain 1 to 10 moles of a complex forming acid which is soluble in polar solvents, per mole of tetrazolium salt. Additionally, the invention provides a process for the detection of reducing materials, wherein a stabilized composition as described is added to a test batch.

12 Claims, No Drawings

STABILIZED COMPOSITION OF TETRAZOLIUM SALTS

This application is a continuation of Ser. No. 871,498, filed 6/6/86, now abandoned, which is a division of Ser. No. 593,192, filed 3/27/84, now U.S. Pat. No. 4,613,569, which is a continuation of Ser. No. 328,315, filed 12/7/81, now abondoned.

This invention relates to a new stabilized preparation of tetrazolium salts for analytical purposes.

Tetrazolium salts have long been known in analytical chemistry for the detection of reducing materials and especially of reduced nicotinamide-adenine dinucleotide (NADH). The transference of hydrogen is catalysed not only by enzymes, such as diaphorase, but also by 5-methylphenazinium methylsulphate (PMS) or similar substances, deep coloured formazanes thereby being formed which permit a very sensitive detection of the reducing substances in visible light. Therefore, appropriate processes have been developed in this way to detect a series of substances which are important in analytical chemistry, via the NADH produced as intermediate. However, a disadvantage of this reaction is that the tetrazolium salts decompose relatively easily, especially in solution, and form coloured decomposition products. Even in the case of storage at low temperature and with the exclusion of light, the stability of such products is limited (see H. U. Bergmeyer, Grundlagen der enzymatischen Analyse, pub. Verlag Chemie, Weinheim, 1977, pp. 91–95, with further references).

Consequently, the problem exists of finding stabilising agents which reduce or remove the sensitivity of the tetrazolium salts to comparatively high temperatures and to light, without influencing the sensitivity of the detection reactions.

Thus, according to the present invention, there are provided stabilized compositions of tetrazolium salts for analytical purposes, wherein they contain 1 to 10 moles and preferably 1 to 2 moles of a complex-forming acid which is soluble in polar solvents per mole of tetrazolium salt.

Conventionally employed tetrazolium salts, such as 3-(4',5'-dimethylthiazolyl-2)-2,4-diphenyltetrazolium bromide (MTT), 2-(p-iodophenyl)-3-(p-nitrophenyl)-5-phenyl-tetrazolium chloride (INT), 2,2',5,5'-tetra-(p-nitrophenyl)-3,3'-(3-dimethoxy-4-diphenylene)-ditetrazolium chloride (TNBT), 2,2'-di-(p-nitrophenyl)-5,5'-diphenyl-3,3'-(3,3'-dimethoxy-4,4'-diphenylene)-ditetrazolium chloride (NBT), 2,2'-p-diphenylene-3,3',5,5'-tetraphenylditetrazolium chloride (neotetrazolium chloride) (NT) and 2,3,5-triphenyltetrazolium chloride (TT) are usually commercially available as chlorides or bromides and have hitherto been used as such in tests. An assumption that these salts hydrolyse partly in solution and that the instability is in some way connected therewith could not be confirmed since an addition of conventional acids does not remove the instability. Conventional strong acids, such as toluenesulphonic acid, oxalic acid or malonic acid, proved to be ineffective.

Surprisingly, we have now found that in part less acidic but complex-forming acids, such as boric acid or organic hydroxypolycarboxylic acids, for example citric acid or malic acid, possess a very considerable stabilising effect not only against temperature stressing of the composition but also against illumination. Solutions of such a composition can, for example, be stored for several days at ambient temperature and in daylight without changing noticeably, i.e. their usefulness for analytical purposes is not lost. Commercially available forms of composition, for example lyophilisates or impregnations on to absorbent carriers (reagent strips) can, after stabilization according to the present invention, from findings which we have already made, be kept for at least a year at ambient temperature without noticeable decomposition.

Since the stabilising agents employed according to the present invention do not disturb the previously known test systems in which tetrazolium salts are used as indicators, this stabilization can be used for all known tests. Thus, for example, mention may be made of the detection of lactic acid with lactate dehydrogenase, alcohol with alcohol dehydrogenase, glycerol with glycerol dehydrogenase, glucose with glucose dehydrogenase, acetaldehyde with acetaldehyde dehydrogenase, as well as further systems which can be coupled to the above system, for example via the formation of hydrogen peroxide and its reaction with alcohol and catalase to give acetaldehyde. Furthermore, strong reducing agents, for example ascorbic acid, can, of course, also reduce tetrazolium salts directly to give the formazane.

The compositions according to the present invention are usually added to the test system in the form of a solution but, for comparatively long term storage, it is recommended to use them in solid form, for example as lyophilisates, powders or tablets or impregnated on to absorbent carriers. Such absorbent carriers can, at the same time, be attached to a short handle so that they can be used as mixing device in the manner described in Federal Republic of Germany Patent Specification No. 2,301,999.

The following Examples are given for the purpose of illustrating the present invention:

EXAMPLE 1

Reagent paper with 3-(4,5-dimethylthiazolyl-2)-2,4-diphenyltetrazolium bromide (MTT)

Filter paper (Schleicher & Schüll No. 598) is impregnated with a solution of the following composition:
MTT: 0.25 mole
citric acid: 0.50 mole
methanol: ad 1000 ml.
and then dried. A lemon yellow material is obtained which, upon elution into water, gives a bright yellow solution with a pH of 2.2 and which, protected against light, is stable for at least one year at ambient temperature.

If a comparison is made with reagent papers prepared in an analogous manner but which contain other acids instead of citric acid in the same mole ratio by measurement in a remission spectrophotometer (Zeiss DMR 21) between 400 and 700 nm., then with increasing period of stressing, a more or less marked coloration is to be observed in the range of from 560 to 580 nm., which is set out in the following Table. The decomposition product is preponderantly formazane.

| acid variant (1 mole acid per 0.5 mole MTT) | pH after elution in water | % remission at 578 nm | | |
|---|---|---|---|---|
| | | unstressed | 12 weeks at 25° C. | 36 weeks at 25° C. |
| without acid | 5.5 | 62 | 60 | 42 |
| tartaric acid | 2.1 | 95 | 80 | 52 |

-continued

| acid variant (1 mole acid per 0.5 mole MTT) | pH after elution in water | % remission at 578 nm | | |
|---|---|---|---|---|
| | | unstressed | 12 weeks at 25° C. | 36 weeks at 25° C. |
| salicylic acid | 2.2 | 67 | 64 | 55 |
| oxalic acid | 1.5 | 85 | 78 | 40 |
| boric acid | 4.5 | 93 | 91 | 80 |
| citric acid | 2.2 | 93 | 90 | 83 |

EXAMPLE 2

Lactate dehydrogenase (LDH) colour test with MTT/diaphorase

On the lower end of a reagent strip of 6 mm. breadth and about 75 mm. length are fixed 3 separate zones with the dimensions 6×6 mm., one of which contains 1.3 mg. MTT, together with 1.3 mg. citric acid impregnated on to filter paper (Schleicher & Schüll No. 3455) from methanolic solution, another contains 4.8 mg. NAD impregnated on to polyamide/cellulose fleece (Binzer No. VS 532) from aqueous solution and the third contains 0.3 U diaphorase impregnated on to polyamide/cellulose fleece (Binzer No. VS 532) from 0.05 molar tris-citrate buffer (pH 7). Elution into 2 ml. of a 0.1 molar tris/HCl solution (pH 8.0) which contains 0.5% detergent and 40 mMol/liter of lactate gives a reagent solution with the following composition:

tris/HCl buffer: 0.1 mol/l.
detergent: 0.5%
lactate: 0.04 mol/l.
NAD: 1.5 mmol/l.
MTT: 1.5 mmol/l.
diaphorase: 130 U/l.
citrate: 6.0 mmol/l.

0.02 ml. of serum is pipetted into 2 ml. of this solution, well mixed and the mixture left to stand for 3 minutes at ambient temperature.

The LDH enzyme reaction is then measured by continuous recording or reading off of the extinction after definite periods of time, for example every 60 seconds.

Reagent test strips stored for a year at ambient temperature with the exclusion of light and moisture show results which are identical to those obtained with freshly prepared reagent strips. The analysis of the component materials gave the following values, referred to one reagent strip:

| component material | unstressed | 6 months at 25° C. | 12 months at 25° C. |
|---|---|---|---|
| NAD | 4.8 mg. | 4.6 mg. | 4.0 mg. |
| diaphorase | 0.3 U | 0.21 U | 0.18 U |
| MTT | 1.3 mg. | 1.3 mg. | 1.2 mg. |
| formazane | 0.0 | 0.0 | 0.0 |

A reagent strip prepared identically except for the addition of citrate buffer and citric acid shows the following analytical values. Even in the case of the unstressed papers, the formazane formed from the MTT disturbs the measurement. After stressing, a measurement is no longer possible:

| component material | unstressed | 6 months at 25° C. |
|---|---|---|
| NAD | 4.8 mg. | 4.6 mg. |
| diaphorase | 0.3 U | 0.21 U |
| MTT | 1.2 | 1.0 |
| formazane | 0.1 | 0.3 |

It will be understood that the specification and examples are illustrative but not limitative of the present invention and that other embodiments within the spirit and scope of the invention will suggest themselves to those skilled in the art.

What is claimed is:

1. A stabilized composition of tetrazolium salts for analytical purposes consisting of tetrazolium salt and 1–10 moles of a complex forming organic hydroxypolycarboxylic acid, which is soluble in polar solvents, per mole of said tetrazolium salt.

2. The composition as claimed in claim 1, containing 1 to 2 moles of said complex-forming organic hydroxypolycarboxylic acid, which is soluble in polar solvents, per mole of tetrazolium salt.

3. The composition as claimed in claim 1, wherein the complex forming organic hydroxypolycarboxylic acid is citric acid.

4. The composition as claimed in claim 1, wherein the tetrazolium salt is 3-(4',5'-dimethylthiazolyl-2)-2,4-diphenyltetrazolium bromide.

5. The composition as claimed in claim 1, wherein the tetrazolium salt is 2-(p-iodophenyl)-3-(p-nitrophenyl)-5-phenyltetrazolium chloride.

6. The composition as claimed in claim 1, wherein the tetrazolium salt is 2,2'-di-(p-nitrophenyl)-5,5'-diphenyl-3,3'-(3,3'-dimethoxy-4,4'-diphenylene)-ditetrazolium chloride.

7. The composition as in claim 1, wherein said composition is a lyophilizate of said tetrazolium salt, said complex-forming organic hydroxypolycarboxylic acid and a polar solvent.

8. A test strip for analytical purposes consisting of an absorbent carrier having impregnated therein a composition which consists of a tetrazolium salt and from 1 to 10 moles of a complex forming organic hydroxypolycarboxylic acid which is soluble in polar solvents, per mole of said tetrazolium salt.

9. A stabilized composition for analytical purposes consisting of a tetrazolium salt, from 1–10 moles of a complex forming organic hydroxypolycarboxylic acid which is soluble in polar solvents, per mole of said tetrazolium salt, and a hydrogen transfer catalyst.

10. The composition of claim 9, wherein said catalyst is diaphorase.

11. The composition of claim 9, wherein said catalyst is 5-methylphenazinium methylsulphate.

12. A stabilized composition of tetrazolium salts for analytical purposes consisting of a tertrazolium salt, 1–10 moles of a complex forming organic hydroxypolycarboxylic acid, which is soluble in polar solvents, per mole of said tetrazolium salt, and a polar solvent in which said hydroxypolycarboxylic acid is soluble.

* * * * *